United States Patent
Raney et al.

(10) Patent No.: US 8,157,750 B2
(45) Date of Patent: Apr. 17, 2012

(54) INTEGRATED ANALYTICAL TEST ELEMENT

(75) Inventors: Charles C. Raney, Camdenton, MO (US); Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 6 days.

(21) Appl. No.: 12/687,920

(22) Filed: Jan. 15, 2010

(65) Prior Publication Data

US 2010/0113978 A1 May 6, 2010

Related U.S. Application Data

(60) Division of application No. 11/691,674, filed on Mar. 27, 2007, now Pat. No. 7,708,703, which is a division of application No. 11/275,592, filed on Jan. 18, 2006, now Pat. No. 7,214,200, which is a continuation-in-part of application No. 10/737,026, filed on Dec. 16, 2003, now Pat. No. 7,211,052.

(60) Provisional application No. 60/437,002, filed on Dec. 30, 2002.

(51) Int. Cl.
- *A61B 5/00* (2006.01)
- *A61B 17/14* (2006.01)
- *A61B 17/32* (2006.01)
- *B65D 81/00* (2006.01)

(52) U.S. Cl. ......... 600/584; 600/583; 600/573; 606/181

(58) Field of Classification Search .................. 600/583, 600/584, 573, 576; 606/181–183
See application file for complete search history.

(56) References Cited

U.S. PATENT DOCUMENTS

| | | | |
|---|---|---|---|
| 3,626,929 A | 12/1971 | Sanz et al. |
| 3,802,842 A | 4/1974 | Lange et al. |
| 4,061,468 A | 12/1977 | Lange et al. |
| 4,360,016 A | 11/1982 | Sarrine |
| 4,490,465 A | 12/1984 | Limbach et al. |
| 4,627,445 A | 12/1986 | Garcia et al. |
| 4,648,408 A | 3/1987 | Hutcheson et al. |

(Continued)

FOREIGN PATENT DOCUMENTS

EP  0 164 148  12/1985

(Continued)

OTHER PUBLICATIONS

Haar et al., U.S. Appl. No. 12/037,197, filed Feb. 26, 2008, "Assembly for Receiving Body Fluids, and Method for the Production Thereof".

(Continued)

*Primary Examiner* — Max Hindenburg
*Assistant Examiner* — Huong Nguyen
(74) *Attorney, Agent, or Firm* — Woodard, Emhardt, Moriarty, McNett & Henry LLP

(57) ABSTRACT

A lancet integrated test element (LIT) includes an incision forming member that has a cutting end configured to form an incision in tissue. A test element is attached to the incision forming member to test fluid from the incision. The test element has a sampling end with a sample opening through which the fluid is collected. The test element is bendable from a first state where the cutting end of the incision forming member is retracted from the sampling end of the test element to a second state where at least a portion of the cutting extends past the sampling end of the test element to form the incision in the tissue.

18 Claims, 5 Drawing Sheets

U.S. PATENT DOCUMENTS

| | | |
|---|---|---|
| 4,653,511 A | 3/1987 | Goch |
| 4,873,993 A | 10/1989 | Meserol et al. |
| 4,883,068 A | 11/1989 | Dechow |
| 4,920,977 A | 5/1990 | Haynes |
| 4,924,879 A | 5/1990 | O'Brien |
| 5,700,695 A | 12/1997 | Yassinzadeh et al. |
| 5,776,719 A | 7/1998 | Douglas et al. |
| 5,824,491 A | 10/1998 | Priest et al. |
| 5,857,983 A | 1/1999 | Douglas et al. |
| 5,868,772 A | 2/1999 | LeVaughn et al. |
| 5,879,311 A | 3/1999 | Duchon et al. |
| 5,951,492 A | 9/1999 | Douglas et al. |
| 5,951,493 A | 9/1999 | Douglas et al. |
| 5,962,215 A | 10/1999 | Douglas et al. |
| 5,964,718 A | 10/1999 | Duchon et al. |
| 6,048,352 A | 4/2000 | Douglas et al. |
| 6,071,250 A | 6/2000 | Douglas et al. |
| 6,071,294 A | 6/2000 | Simons et al. |
| 6,086,545 A | 7/2000 | Roe et al. |
| 6,093,156 A | 7/2000 | Cunningham et al. |
| 6,099,484 A | 8/2000 | Douglas et al. |
| 6,143,164 A | 11/2000 | Heller et al. |
| 6,183,489 B1 | 2/2001 | Douglas et al. |
| 6,319,210 B1 | 11/2001 | Douglas et al. |
| 6,332,871 B1 | 12/2001 | Douglas et al. |
| 6,551,494 B1 | 4/2003 | Heller et al. |
| 6,561,989 B2 | 5/2003 | Whitson |
| 6,607,658 B1 | 8/2003 | Heller et al. |
| 6,618,934 B1 | 9/2003 | Feldman et al. |
| 6,623,501 B2 | 9/2003 | Heller et al. |
| 6,849,052 B2 | 2/2005 | Uchigaki et al. |
| 6,866,675 B2 | 3/2005 | Perez et al. |
| 7,211,052 B2 | 5/2007 | Roe |
| 7,214,200 B2 | 5/2007 | Raney et al. |
| 7,264,627 B2 | 9/2007 | Perez |
| 2001/0037099 A1 | 11/2001 | Effenhauser |
| 2002/0052618 A1 | 5/2002 | Haar |
| 2002/0137998 A1 | 9/2002 | Smart et al. |
| 2002/0168290 A1 | 11/2002 | Yuzhakov et al. |
| 2002/0169393 A1 | 11/2002 | Cunningham et al. |
| 2002/0188224 A1 | 12/2002 | Roe et al. |
| 2003/0018282 A1 | 1/2003 | Effenhauser et al. |
| 2003/0050573 A1 | 3/2003 | Kuhr et al. |
| 2003/0144608 A1 | 7/2003 | Kojima et al. |
| 2003/0212347 A1 | 11/2003 | Sohrab |
| 2004/0064068 A1 | 4/2004 | DeNuzzio et al. |
| 2004/0106941 A1 | 6/2004 | Roe |
| 2004/0127818 A1 | 7/2004 | Roe |
| 2004/0127819 A1 | 7/2004 | Roe et al. |
| 2004/0127929 A1 | 7/2004 | Roe |
| 2004/0186394 A1* | 9/2004 | Roe et al. ............... 600/583 |
| 2004/0193072 A1 | 9/2004 | Allen |
| 2004/0215224 A1 | 10/2004 | Sakata et al. |
| 2005/0008537 A1 | 1/2005 | Mosoiu et al. |
| 2005/0013731 A1 | 1/2005 | Burke et al. |
| 2005/0016844 A1 | 1/2005 | Burke et al. |
| 2005/0019212 A1 | 1/2005 | Bhullar et al. |
| 2005/0021066 A1 | 1/2005 | Kuhr et al. |
| 2005/0033341 A1* | 2/2005 | Vreeke et al. ............ 606/181 |
| 2005/0036909 A1 | 2/2005 | Erickson et al. |
| 2005/0103624 A1 | 5/2005 | Bhullar et al. |
| 2005/0251064 A1 | 11/2005 | Roe |
| 2005/0261716 A1 | 11/2005 | Sakata et al. |
| 2005/0277850 A1 | 12/2005 | Mace et al. |
| 2005/0283094 A1 | 12/2005 | Thym et al. |
| 2005/0288698 A1 | 12/2005 | Matsumoto |
| 2006/0079810 A1 | 4/2006 | Patel et al. |
| 2006/0100543 A1 | 5/2006 | Raney et al. |
| 2006/0174592 A1 | 8/2006 | Chan |
| 2006/0200045 A1 | 9/2006 | Roe |
| 2006/0229532 A1 | 10/2006 | Wong et al. |
| 2006/0293611 A1 | 12/2006 | Calasso |
| 2007/0016103 A1 | 1/2007 | Calasso |
| 2007/0038149 A1 | 2/2007 | Calasso |
| 2007/0167869 A1 | 7/2007 | Roe |
| 2007/0173739 A1 | 7/2007 | Chan |
| 2007/0173740 A1 | 7/2007 | Chan et al. |
| 2007/0191738 A1 | 8/2007 | Raney |
| 2007/0191739 A1 | 8/2007 | Roe |
| 2008/0097244 A1 | 4/2008 | Arnitz |
| 2008/0103415 A1 | 5/2008 | Roe et al. |
| 2008/0161724 A1 | 7/2008 | Roe |

FOREIGN PATENT DOCUMENTS

| | | |
|---|---|---|
| EP | 0 894 471 | 2/1999 |
| EP | 1 238 632 A1 | 9/2002 |
| EP | 1 402 812 A1 | 3/2004 |
| WO | WO 93/09710 A1 | 5/1993 |
| WO | WO 97/08986 A1 | 3/1997 |
| WO | WO 98/15810 A1 | 4/1998 |
| WO | WO 02-17804 A | 1/2002 |
| WO | WO 02/56751 A2 | 7/2002 |
| WO | WO 2004/064636 A1 | 8/2004 |
| WO | WO 2004/086970 A1 | 10/2004 |
| WO | WO 2005/084530 A2 | 9/2005 |
| WO | WO 2005/084545 A1 | 9/2005 |
| WO | WO 2005/084546 A2 | 9/2005 |
| WO | WO 2005/104948 A1 | 11/2005 |
| WO | WO 2006/005503 A1 | 1/2006 |
| WO | WO 2007/147494 A2 | 12/2007 |

OTHER PUBLICATIONS

Haar et al., U.S. Appl. No. 12/105,596, filed Apr. 18, 2008, "Analytical System for Detecting an Analyte in a Body Fluid and Disposable Integrated Puncturing and Analyzing Element".

International Application No. PCT/EP2007/000354, "International Preliminary Report on Patentability", mailed Jul. 22, 2008.

Joseph et al., U.S. Appl. No. 12/177,328, filed Jul. 22, 2008, "Method and Apparatus for Lighted Test Strip".

Joseph et al., U.S. Appl. No. 12/180,101, filed Jul. 25, 2008, Method for Manufacturing a Sterilized Lancet Integrated Biosensor.

Wong et al., U.S. Appl. No. 12/020,766, filed Jan. 28, 2008, "Rapid Blood Expression and Sampling".

European Patent Application 03 814 825.0 Examination Report mailed Apr. 14, 2010.

* cited by examiner

INTEGRATED ANALYTICAL TEST ELEMENT

REFERENCE TO RELATED APPLICATIONS

The present application is a divisional of U.S. patent application Ser. No. 11/691,674, filed Mar. 27, 2007 now U.S. Pat. No. 7,708,703, which is a divisional of U.S. patent application Ser. No. 11/275,592, filed Jan. 18, 2006, now U.S. Pat. No. 7,214,200, which is a continuation-in-part of U.S. patent application Ser. No. 10/737,026, filed Dec. 16, 2003, now U.S. Pat. No. 7,211,052, which claims the benefit of U.S. Provisional Application No. 60/437,002, filed Dec. 30, 2002, which are hereby incorporated by reference in their entirety.

BACKGROUND

The present invention generally relates to bodily fluid sampling devices and more specifically, but not exclusively, concerns a lancet integrated test element with a flexible test element that bends during lancing in order to allow a lancet to pierce the skin or other tissue.

The acquisition and testing of bodily fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

The testing of bodily fluids basically involves the steps of obtaining the fluid sample, transferring the sample to a test device, conducting a test on the fluid sample, and displaying the results. These steps are generally performed by a plurality of separate instruments or devices. Performing these steps can be difficult for patients, especially for patients with limited hand dexterity, such as the elderly, or those suffering the affects of their condition, like diabetes. Diabetics suffer many symptoms that can make self-monitoring difficult. For example, diabetics can sometimes experience numbness or tingling in their extremities, such as their hands, and also wounds tend to heal more slowly for diabetics. In a typical procedure, the patient first creates an incision in the skin by lancing the skin with a lancet. In order to ensure that a sufficient number of capillaries are cut for supplying an adequate bodily fluid sample, the incision has to usually be deep, which can be rather painful for the patient. Often the incision still does not provide an adequate amount bodily fluid for the sample, and the patient then must resort to expressing the fluid from the incision. If during expression of the fluid the patient is not careful, smearing of the fluid can occur, which may result in rendering the sample useless. Once a sufficient amount of fluid collects as a droplet on the skin, the patient has to position a test strip over the site such that the test strip contacts and absorbs a sufficient amount of the droplet for testing. Usually the droplet of fluid is quite small, and patients, especially ones with hand motor control problems, may experience great difficulty in positioning the test strip so as to collect a sample from the droplet. As should be appreciated, patients can become frustrated by this procedure, and consequently, they may perform the test less often or may even quit testing altogether.

Recently, lancet integrated test elements, or LITs, have been developed in which a test strip is integrated with a lancet so as to form a single disposable unit. While these integrated units have somewhat simplified the collection and testing of fluid samples, there are still a number of issues that need to be resolved before a commercial unit can be implemented. One issue concerns the interaction between the lancet and the test strip during fluid collection. In one type of design, the lancet is fixed relative to the test strip and extends past the edge of the test strip. During lancing, the entire integrated lancing test strip is fired by a lancing mechanism to form an incision, and after forming the incision, the entire integrated lancing test strip is typically retracted from the skin so that the blade is removed from the incision in order to promote blood flow as well as to dull the pain.

With the lancet fixed relative to the strip, a number of difficulties in sampling the fluid are created. For instance, as noted before, the lancet typically extends from the test strip near the capillary opening for the test strip. At such a position, the blade of the lancet can interfere with the collection of body fluid by smearing the droplet of blood on the skin and/or by drawing blood away from the capillary channel. Further, the distance that the capillary has to be retracted is directly proportional to the length of the lancet blade that extends from the test strip. The greater penetration depth created by longer lancet blades usually increases the amount of blood that is bled from the incision, but the greater length of the lancet necessitates that the test strip be retracted farther away from the skin, which in turn can reduce the chances that the blood will be successfully drawn into the capillary channel of the test strip. Conversely, shorter lancets reduce the distance of the test strip from the skin, but shorter lancets normally produce smaller fluid sample sizes from the incision. Moreover, retraction of the entire integrated device is sometimes inconsistent, thereby leading to some undesirable consequences. If the integrated device is retracted too far from the skin, the capillary channel might not be able to contact the fluid droplet on the skin, thereby resulting in an incomplete test or insufficient sample size for testing. The fixed lancet can also interfere with fluid collection because the fluid will tend to wick up the lancet during fluid collection.

To alleviate some of these difficulties, LITs have been developed in which the lancet is moveable relative to the test element. In one typical design, the lancet is coupled to a test strip via a metal spring. After the lancet is fired and the incision is formed, the spring is used to retract the lancet from the incision. However, such designs still have a number of drawbacks. For example, the flexible nature of the spring can complicate manufacturing by creating greater component variance when aligning the lancet with the test element. Also, packaging and maintaining the sterility of the lancet and test strip is complicated by the spring. With the spring, the lancet can easily extend, which can lead to accidental cuts and exposure of the lancet. Moreover, forming the spring adds expense to manufacturing, and the spring can be prone to damage during handling. If the spring is damaged or the lancet is misaligned, the lancet might not fully retract, which can lead to a number of difficulties. For instance, part of the lancet might remain in the incision after lancing, which can be quite painful to the user. Even when the lancet does not remain in the incision, the lancet tip can still extend past the end of the test element so as to disrupt fluid collection. With the lancet tip extending past the end of the test element, the body or biological fluid, such as blood, will tend to first wick up the lancet, thereby wasting the fluid. Due to the rigid nature of the test strip, if the test strip is pressed too hard against the skin, fluid flow from the incision can become constricted. Thus, needs remain for further contributions in this area of technology.

SUMMARY

One aspect concerns an integrated device. The integrated device includes an incision forming member that has a cutting end configured to form an incision in tissue. A test element is attached to the incision forming member to test fluid from the incision. The test element has a sampling end with a sample opening through which the fluid is collected. The test element is bendable from a first state where the cutting end of the incision forming member is retracted from the sampling end of the test element to a second state where at least a portion of the cutting extends past the sampling end of the test element to form the incision in the tissue.

Another aspect concerns an apparatus that includes an integrated lancing test device and a lancing mechanism. The integrated lancing test device includes an incision forming member configured to form an incision in tissue. A test element is attached to the incision forming member for testing fluid from the incision. The test element is bendable to expose the incision forming member during formation of the incision. The lancing mechanism includes a holder to which the integrated device is coupled. The holder includes one or more stops to prevent excessive bending of the test strip during lancing.

Still yet another aspect concerns a technique in which a lancet integrated test strip is provided that includes a lancet attached to a test strip. A cutting end of the lancet extends proximal a sampling end of the test strip that includes a sample chamber opening. An incision is formed in tissue with the lancet integrated test strip, and the test strip bends by pressing the sampling end of the test strip against the tissue to extend the cutting end of the lancet past the sampling end of the test strip and into the tissue. Fluid from the incision is sampled by drawing fluid into the sample chamber opening of the test strip.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
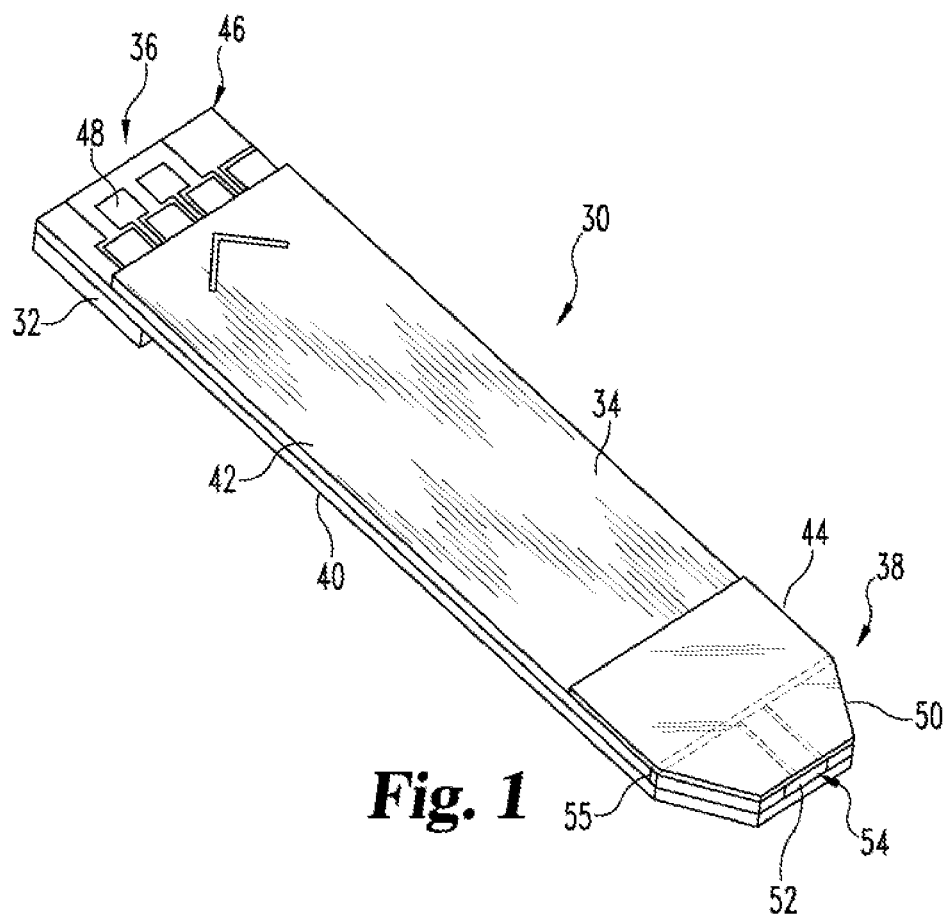
FIG. 1 is a top, perspective view of a lancet integrated test element or device according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail; although it will be apparent to those skilled in the relevant art that some features that are not relevant to the present invention may not be shown for the sake of clarity.

As will be discussed in greater detail below, a lancet is integrated with a test strip to form an integrated device or disposable that is used to sample and analyze biological fluids, like blood and/or interstitial fluid. In the integrated device, the lancet is generally rigid, while the test strip is flexible. The flexible nature of the test strip allows the test strip to bend when fired against the skin during lancing. Contrary to some views, it was discovered that the test strip could be bent without incurring any significant damage to the test strip. As the test strip bends or arches against the skin, the tip of the lancet is able to extend past the end of the test strip to form an incision in the skin. In one form, the integrated device is mounted in a holder of a lancing mechanism, and the holder prevents the test strip from being bent too far during lancing. When the lancet is retracted from the incision, the test strip straightens and is able to collect blood or other fluids from the incision. The resilient nature of the test strip helps to reduce the chance of constricting the fluid flow from the incision when the test strip is pressed against the skin. As will be recognized, manufacturing of the device is greatly simplified because the need for a separate spring for retracting the lancet is eliminated.

A lancet integrated test element (LIT) or device 30 according to one embodiment, among many embodiments, will now be described with reference to FIGS. 1 and 2. As can be seen, the integrated device 30 includes an incision forming member 32 (FIG. 2) for forming an incision in tissue and a test element or sensor 34 for testing body or biological fluids, such as blood, interstitial fluid as well as other fluids, from the incision. In the illustrated embodiment, the test element 34 is in the form of a flat electrochemical test strip. In one particular form, the test strip 32 includes an ACCU-CHEK® AVIVA brand test strip (Roche Diagnostics Corporation, Indianapolis, Ind.), but it is envisioned that other types of testing means can be used. For example, the test element can include an optical test strip, an electrochemical test strip, or a combination thereof, to name a few. The test element 34 for the embodiment of FIG. 1 will be described with reference to an electrochemical test strip, but again, it should be stressed that the test element 34 can include other testing means, like optical test strips. For the sake of clarity as well as brevity, the various components of the test element 34 in FIG. 1 and techniques for manufacturing the test element 34 will not be described in great detail below, but reference is made to U.S. Patent Application Publication Nos.: 2005/0008537 A1 to Mosoiu et al., published Jan. 13, 2005 (U.S. application Ser. No. 10/871,966, filed Jun. 18, 2004); 2005/0013731 A1 to Burke et al., published Jan. 20, 2005 (U.S. application Ser. No. 10/871,468, filed Jun. 18, 2004); 2005/0016844 A1 to Burke et al., published Jan. 27, 2005 (U.S. application Ser.

No. 10/871,673, filed Jun. 18, 2004); 2005/0019212 A1 to Bhullar et al., published Jan. 27, 2005 (U.S. application Ser. No. 10/872,027, filed Jun. 18, 2004); and 2005/0103624 A1 to Bhullar et al., published May 19, 2005 (U.S. application Ser. No. 10/871,937, filed Jun. 18, 2004), which are hereby incorporated by reference in their entirety.

Figure 2:
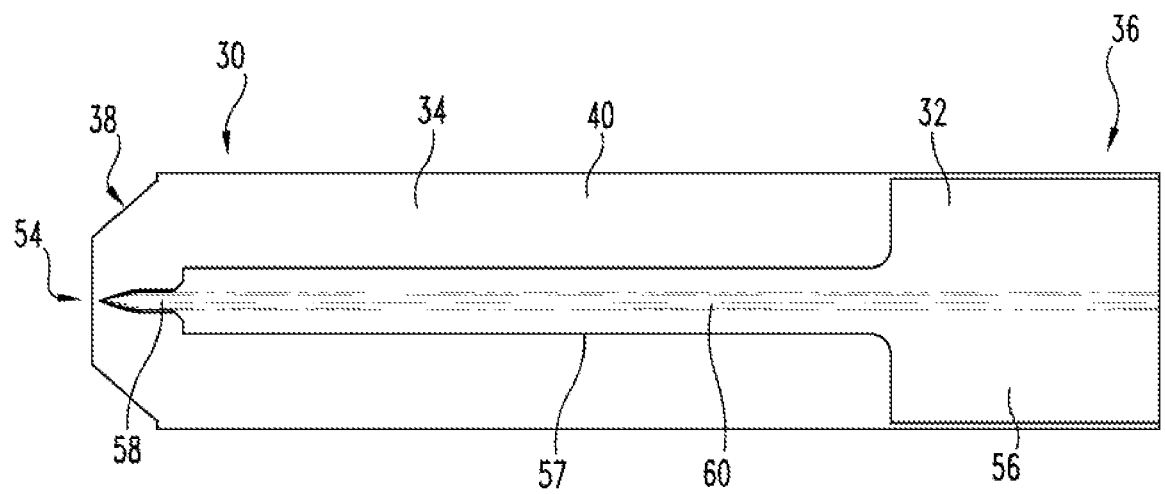
FIG. 2 is a bottom view of the FIG. 1 integrated device.

Looking at FIGS. 1 and 2, the integrated device 30 includes a connector or contact end portion 36 where the test element 34 is coupled to a meter and a sampling (dosing) end portion 38 where the fluid sample is collected. The test element 34 in the illustrated embodiment is generally flat and has the form of a strip, but it should be realized that the test element 34 in other embodiments can be shaped differently. In the embodiment depicted, the test strip 32 has a laminar construction, but it is envisioned that the test strip 34 can have a different construction in other embodiments.

Turning to FIG. 1, the test strip 34 includes a base substrate 40, a spacer layer 42 and a cover layer 44. The base substrate 40 supports an electrode system 46 that includes a plurality of electrodes with electrode traces that have contact pads 48 at the contact end portion 36 of the integrated device 30. A meter and/or other electronics are operatively coupled to the test strip 34 via the contact pads 48. At the sampling end portion 38, the spacer layer 42 has a sample notch 50 that together with the base 40 and cover 44 layers forms a sample chamber 52. Further, at the sampling end portion 38, the sample chamber 52 has a sample chamber opening 54 through which the fluid sample is received into the sample chamber 52. In one form, the sample chamber 52 is sized to draw fluid via capillary action, but it is envisioned that the fluid can be drawn in other manners, like via suction. The sample chamber 52 as well as the sample chamber opening 54 can have portions that are hydrophobic and/or hydrophilic so as to direct the fluid flow. The sample chamber opening 54 is positioned so as to be able to collect fluid from the incision formed by the lancet 32. In the illustrated embodiment, the sample chamber opening 54 is located for end dosing purposes, but depending on the relative location of the incision forming member 32, it is contemplated that the sample chamber opening 54 can be located elsewhere. For example, the sample chamber opening 54 can be positioned for side and/or top dosing. The test strip 34 further incorporates a vent slot 55 for venting air and/or other gases from the sample chamber 52 as the fluid fills the sample chamber 52. It should be recognized that other types of venting structures can be used in other embodiments.

Inside, the sample chamber 52 includes at least one reagent and electrodes for analyzing the fluid sample. As should be appreciated, the electrodes in the sample chamber 52 are part of the electrode system 46, and the electrodes in the sample chamber 52 are operatively coupled to the contact pads 48 via the traces. Various electrode configurations in the electrode system 46 can be used to analyze the fluid sample. For example, the electrode system 46 can includes various combinations of working, counter, and/or reference electrodes. In conjunction with the reagent, the electrodes are configured to detect the presence of, and/or measure the concentration of, at least one analyte by way of electrochemical oxidation and reduction reactions within the sample chamber 52. These reactions are transduced to an electrical signal that can be correlated to an amount or concentration of the analyte, such as via coulometric, amperometric, voltammetric, and other techniques. Again, it should be recognized that the fluid sample in other embodiments can be analyzed in other manners, such as through optical techniques.

Figure 3:
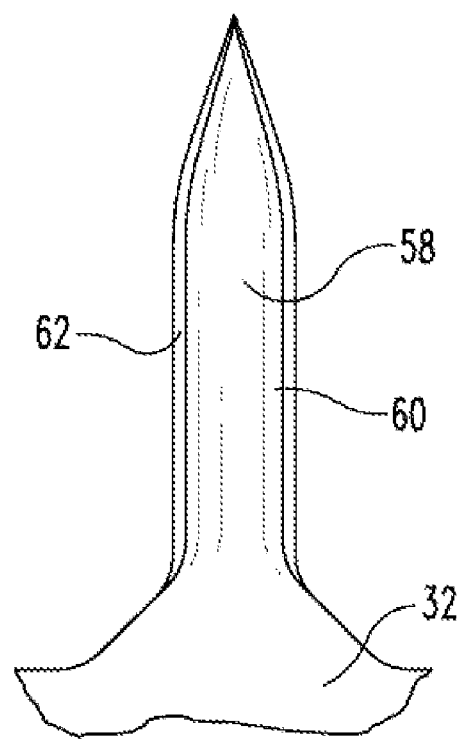
FIG. 3 is an enlarged view of the end of a lancet for the FIG. 1 integrated device.
Figure 4:
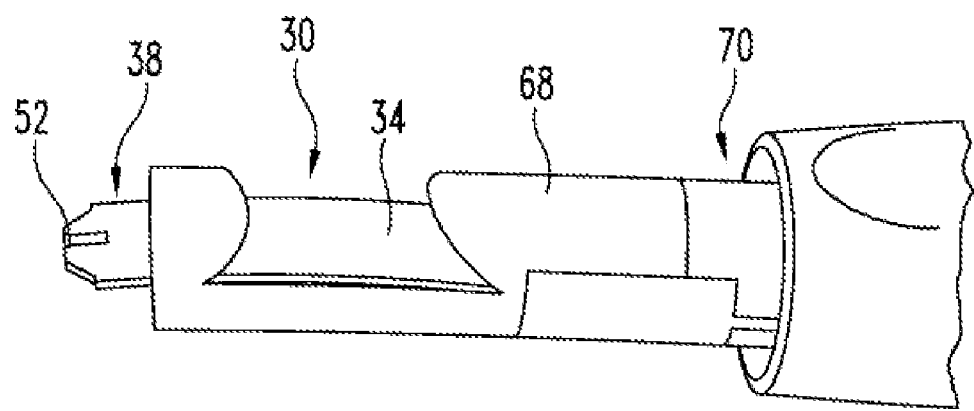
FIG. 4 is a perspective of the FIG. 1 integrated device loaded in a firing mechanism.
Figure 5:
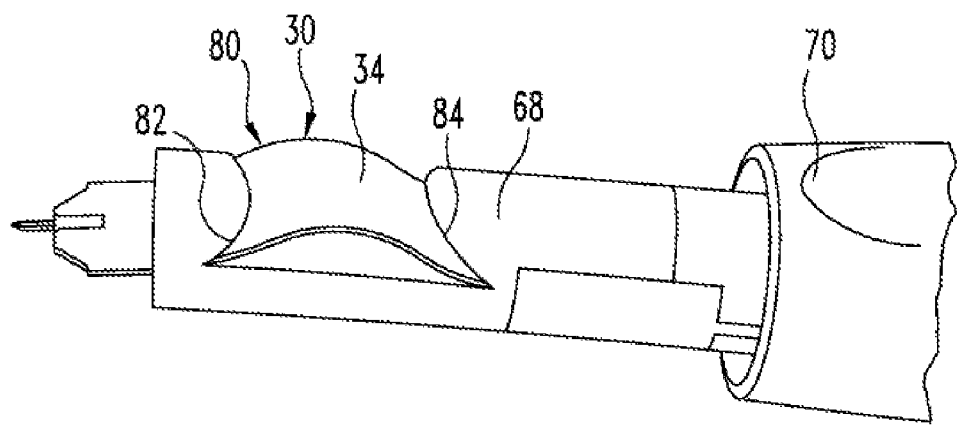
FIG. 5 is a perspective of the FIG. 1 integrated device during lancing.
Figure 6:
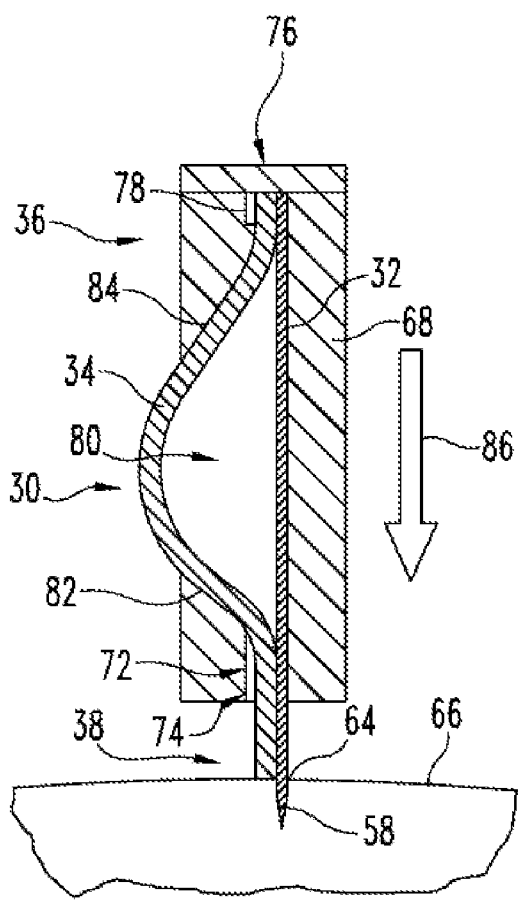
FIG. 6 is a side cross-sectional view of the FIG. 1 integrated device during lancing.
Figure 7:
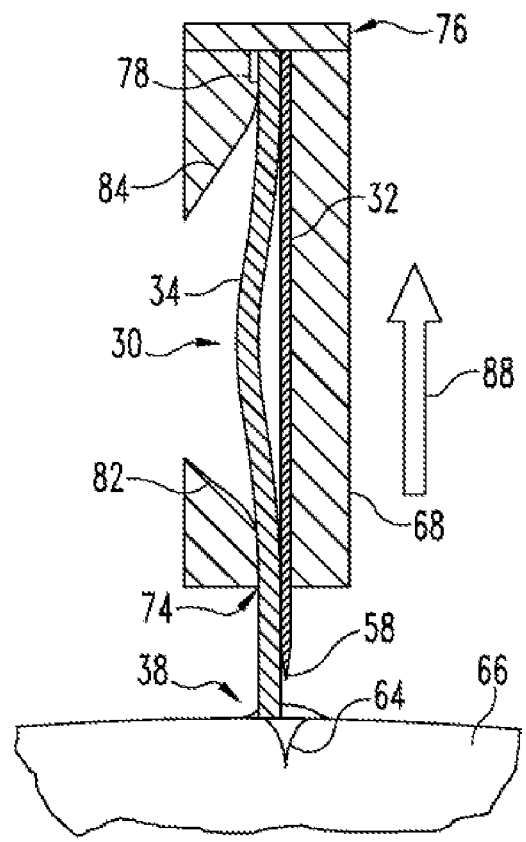
FIG. 7 is a side cross-sectional view of the FIG. 1 integrated device during sampling.

The integrated device 30 shown in the drawings eliminates the need for a separate spring for retracting the incision forming member 32 relative to the test strip 34 after lancing the tissue. In place of the spring, the integrated device 30 utilizes the resilient nature of the test strip 34 such that the test strip 34 is able to bend during lancing and then return to its original generally unbent state after use. With reference to FIGS. 2 and 3, the incision forming member 32 in the illustrated embodiment is in the form of a lancet that is attached to the contact end portion 36 of the test strip 34. Although the incision forming member 32 in the illustrated embodiment will be described with reference to a lancet, it should be appreciated that other types of incision forming devices or means, like needles and blades, can be incorporated into other embodiments. As depicted in FIGS. 4, 5, 6, and 7, the test strip 34 is configured to flex during lancing so that the lancet 32 is exposed for cutting an incision in the tissue (FIGS. 5 and 6). Due to the resilient nature of the test strip 34, after forming the incision, the test strip 34 springs back to its original extended state (FIGS. 4 and 7).

As mentioned previously, the test strip 34 in the illustrated embodiment has a generally laminar structure. The base substrate 40, which in one embodiment is made of an insulating material, supports the electrode system 46 along with other components of the test strip 34. In one embodiment, the base substrate 40 is made of one or more plastics, like vinyl polymers, polyimides, polyesters, and styrenes. In one form, the base substrate 40 can be selected as a flexible polymeric material such as polyester, especially high temperature polyester materials; polyethylene naphthalate (PEN); and polyimide, or mixtures of two or more of these. Polyimides are available commercially, for example under the trade name Kapton®, from E.I. DuPont de Nemours and Company of Wilmington, Del. (DuPont). In one form, the base substrate material is MELINEX® 329 available from DuPont. Nevertheless, it should be recognized that the base substrate 40 as well as other components can be made from different materials. In order to enhance flexibility, the test strip 34 has the base substrate 40 made of 0.005" thick MELINEX® instead of 0.010" thick MELINEX® that is found on some typical test strips, but it again should be appreciated that the thickness of the test strip 34 as well as its various components can be different in other embodiments.

Returning to FIG. 2, the lancet 32 has a test strip attachment portion 56 where the lancet 32 is secured to the test strip 34. In the illustrated embodiment, the lancet 32 is attached to the base substrate 40, but it is contemplated that the lancet 32 can be coupled elsewhere, such as to the spacer layer 42 or along the side edges of the integrated device 30, to name just a few examples. The lancet 32 further includes a shaft portion 57 that extends from portion 56 and a cutting end or tip 58 configured to form an incision. A rib 60 extends along the length of the lancet 32 from the tip 58 to the test strip attachment portion 56. The rib 60 stiffens the lancet 32 as well as the rest of the integrated device 30. The added stiffness provided by the rib 60 reduces the chance of the lancet 32 buckling or bending during lancing. In addition to stiffening the lancet 32, the shape of the rib 60 at the tip 58 of the lancet 32 creates a u-shaped incision or flap during lancing. Nevertheless, it is contemplated that the lancet 32 can be shaped differently in other embodiments. By way of example, the rib 60 can be optional in other embodiments such that the lancet 32 can incorporate other stiffening structures and/or can have an overall flat shape. As can be seen in FIG. 2, the end of the tip 58 is normally recessed back, away from the end of the test strip 34 so that the lancet 32 does not interfere with fluid collection by the test strip 34. For instance, if the tip 58 of the lancet 32 extended past the end of the test strip 34 during sampling, the fluid could be wicked away from sample chamber 54 by the lancet 32 and/or smeared by the lancet 32, thereby inhibiting fluid collection.

In one form, the test strip attachment portion 56 is attached to the contact end 36 of the test strip 34 via an adhesive, but it is envisioned that lancet 32 can be attached in other manners, such as through a mechanical fastener. The test strip attachment portion 56 in other embodiments can be attached at other locations along the test strip 34. The relative stiffness of the test strip 34 can be adjusted based on where the lancet 32 is attached to the test strip 34. For instance, when the lancet 32 is attached closer to the sampling end 38, the test strip 34 will become generally stiffer. By having the ability to adjust the resiliency of the test strip, the integrated device 30 can be adapted for different sampling situations. For example, the stiffness of the test strip 34 can be selected such that the test strip 34 is able to extend to collect a fluid sample, but the test strip 34 is not too stiff such that it presses too hard against the tissue so as to constrict bleeding from the incision. The test strip attachment portion 56 of the lancet 32 in the illustrated embodiment is disposed opposite the contacts 48 on the substrate base 40. With such a construction, the test strip attachment portion 56 is able to stiffen the base substrate 40 underneath the contacts 48 so that the contacts 48 remain connected with the meter as the rest of the test strip 34 bends. In the embodiment shown, portion 56 has a generally rectangular shape, but the test strip attachment portion 56 can have a different shape in other embodiments.

Figure 8:
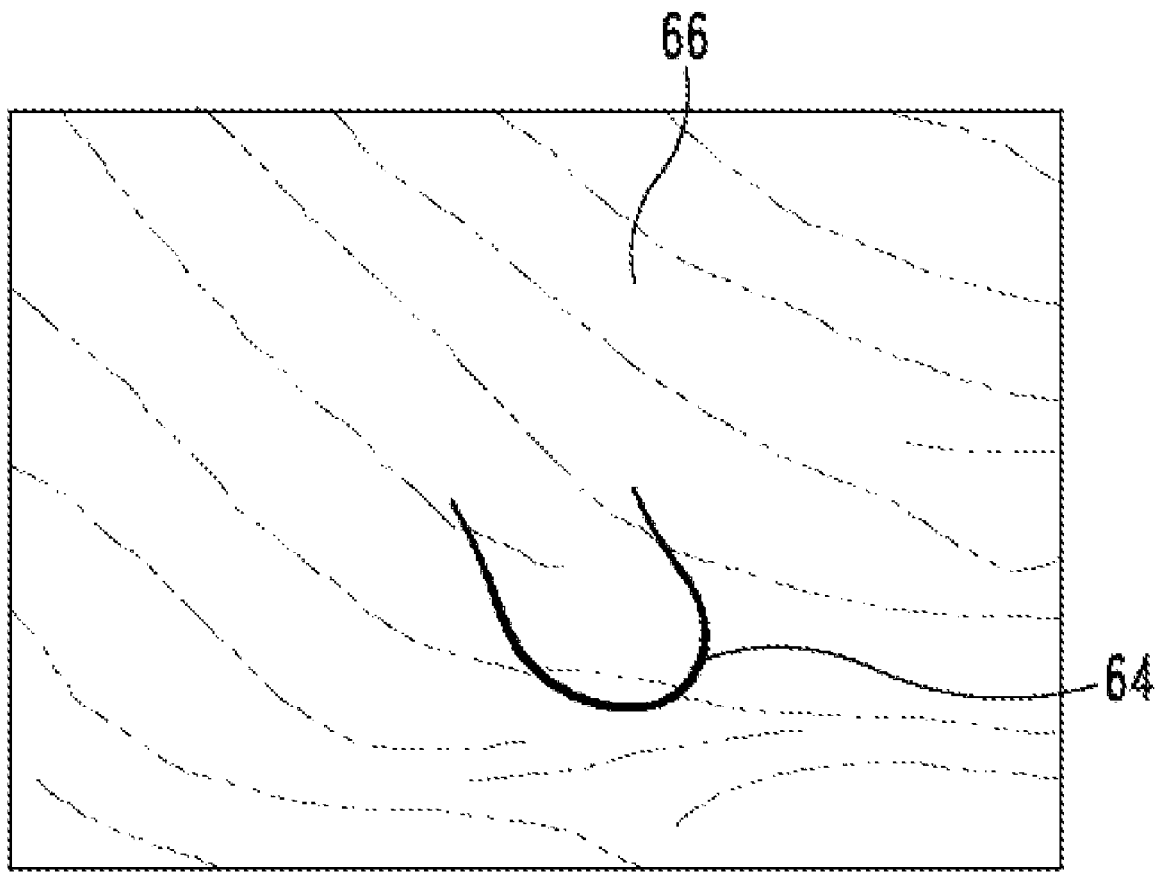
FIG. 8 is a top view of an incision formed by the FIG. 3 lancet.

FIG. 3 shows an enlarged view of the tip 58 of the lancet 32. As can be seen, the rib 60 forms a u-shaped (or arc shaped) channel 62 in the tip 58 of the lancet 32. Consequently, the lancet 32 forms a u-shaped (or arc shaped) incision or flap 64 in tissue 66 during lancing, as is depicted in FIG. 8. It has been discovered that the u-shaped or flap shaped incision 64 promotes bleeding, while at the same time, minimizes the pain associated with lancing. It is theorized that u-shaped incision 64 cuts a greater number of capillaries in comparison to a straight cut, and the incision 64 forms a skin flap, which promotes bleeding.

A perspective view of the integrated device 30 loaded into a holder 68 of a lancing mechanism or lancet driver 70 according to one embodiment is illustrated in FIG. 4. As shown, the lancing mechanism 70 is coupled to the holder 68, and the holder 68 is configured to promote bending of the test strip 34 during lancing, while preventing excessive bending of the test strip 34 that could damage the test strip 34. The lancing mechanism 70 is configured to extend and retract the holder 68 during lancing, and the lancing mechanism 70 can include lancing or other types of actuation mechanisms as would occur to those skilled in the art. For instance, the lancing mechanism 70 can be a spring driven type system and/or an electrically driven system. In one embodiment, the lancing mechanism 70 is a mechanical type lancing mechanism of the type described in U.S. Pat. No. 6,419,661 to Kuhr et al., which is hereby incorporated by reference in its entirety. In one form, the lancing mechanism 70 is incorporated into a meter with a display and/or other output means for providing the results for the analyzed fluid sample.

Looking at FIGS. 6 and 7, the integrated device 30 is slidably received into a holder slot 72 that is defined in the holder 68. The holder slot 72 has an opening 74 through which the sampling end portion 38 of the integrated device 30 extends. Opposite opening 74, the holder slot 72 has a closed end 76 in which the contact end portion 36 of the integrated device 30 is received. To hold the integrated device 30, the closed end 76 is sized in a manner such that the integrated device 30 is frictionally held in the holder 68. During lancing, the closed end 76 of the holder 68 pushes against the end of the integrated device 30 so as to actuate the integrated device 30. It, however, is contemplated that the integrated device 30 can be held in place in different manners such that the holder 68 has a different configuration. By way of nonlimiting examples, the holder 68 in other embodiments can include a clamp, detent, and/or other types of securing devices. In other examples, the closed end 76 can be optional such that the holder 68 can be open at both ends and can use a different structure to hold the integrated device 30 in place. At the closed end 76, the holder 68 has contacts 78 that engage corresponding contacts 48 on the test strip 34. The contacts 78 in the holder 68 transmit the readings and/or other information from the test strip 34 to the meter and/or other devices.

Between the open 74 and closed 76 ends, the holder 68 has a deflection or relief cavity 80 in which the test strip 34 bends during lancing. As can be seen in the drawings, the holder 68 has opposing support or stop surfaces 82, 84 that define the deflection cavity 80. The first stop surface 82 and second stop surface 84 are obliquely angled in an opposite manner such that the test strip 34 bends to form an arch during lancing. The support surfaces 82, 84 prevent the test strip 34 from excessively bending during lancing, which if not addressed, could damage the test strip 34. For instance, the electrodes and traces within the test strip could be damaged if bent to a great degree, and further, if the test strip 34 forms a crease or is folded as it is bent, the test strip 34 might not be able to return to its original extended position. As should be appreciated, the support surfaces 82, 84 prevent excessive bending, thereby allowing the test strip 34 to bend during lancing and spring back generally to its initial extended state when the fluid is sampled. Although test strip 34 in the illustrated embodiment bends in an arched shape, the test strip 34 in other embodiments can bend in different manners. For instance, the test strip 34 in another embodiment can incorporate weakened sections that allow the test strip to bend or fold in an accordion like manner. Furthermore, the deflection cavity 80 of the holder 68 can be shaped differently in other embodiments. By way of a non-limiting example, the deflection cavity 80 in another embodiment can be enclosed by an arched shaped support wall that supports the test strip 34 during bending.

A technique, according to one embodiment, for obtaining, sampling, and analyzing a fluid sample with the integrated device 30 will now be described with reference to FIGS. 4, 5, 6 and 7. Before use, as is depicted in FIG. 4, the integrated device 30 is loaded into the holder 68 of the lancing mechanism 70 by sliding the integrated device 30 into the holder slot 72. If so desired, a lancet cap with a sample opening is attached to the lancing mechanism so as to enclose the integrated device 30 as well as the holder 68. As can be seen, when the integrated device 30 is loaded, the test strip 34 is in an initial, undeflected state with the test strip 34 extending in a straight manner past the tip 58 of the lancet 32.

During lancing, the lancing mechanism 70 fires or moves the holder 68 toward the skin 66, as indicated by arrow 86 in FIG. 6. Once the sampling end 38 contacts the skin 66, the test strip 34 starts to bend in the manner as illustrated in FIGS. 5 and 6. While the test strip 34 flexes, the tip 58 of the lancet 32 is able to extend past the sampling end 38 of the test strip 34 and pierce the skin 66. As previously noted, the support surfaces 82, 84 in the holder 68 brace the test strip 34 during bending to prevent the detrimental affects of excessive bending of the test strip 34.

After forming the incision 64, the lancing mechanism 70 moves or retracts the holder 68 away from the skin 66, as is depicted with arrow 88 in FIG. 7. During retraction, the test strip 34 straightens as the lancet 32 is pulled away from the incision 64. In the illustrated embodiment, the lancet tip 58 retracts out of the incision 64 and behind the end 38 of the test strip 34 so as to minimize interference with fluid collection. In other embodiments, all or part of the lancet tip 58 can remain inside the incision 64 so as to brace the incision 64 open during fluid collection. In such a case, if so desired, the lancet 32 can be made hydrophobic and/or coated with hydrophobic material in order to minimize wicking of fluid up the lancet 32. In some instances, once the holder 68 is fully retracted, the test strip 34 might remain slightly bent (and not be completely straight) due to material memory or due to the test strip 34 being pressed against the skin. With the test strip 34 being resilient, constriction of fluid flow due to over compression of the test strip 34 against the skin can be avoided because the test strip 34 is able to bend. In other embodiments, the end of the test strip 34 can be spaced slightly away from the skin 66 so as to avoid constriction of the fluid flow. Fluid from the incision 64 is drawn into the sample chamber 52 for analysis. After the meter detects that a sufficient amount of fluid has been collected for analysis, the meter in one form can signal that it is safe to remove the meter from the skin 66. The meter analyzes the fluid sample in the sample chamber 52, and the results are displayed on the meter.

As should be appreciated, the above discussed design for the integrated device 30 helps to simplify manufacturing as well as packaging. The test strip 34 and lancet 32 can be readily attached together, and the need for a separate spring or complicated lancet retraction mechanism is eliminated. For example, multiple test strips 34 and lancets 32 can be attached together in a continuous process. Strips of test strips 34 and lancets 32 are rolled from separate rolls and then attached together. The combined strips can be cut to form individual integrated devices 30 or left attached together for use in a reel-to-reel cassette, for example. Although the drawings show only individual integrated devices 30, it should be recognized that multiple integrated devices 30 can be attached, grouped, or otherwise associated together in, for example, drums, cartridges, cassettes, and the like. Moreover, other types of preexisting test strip designs that are already marketed can be easily converted to integrated devices similar to the types shown in the drawings.

Figure 9:
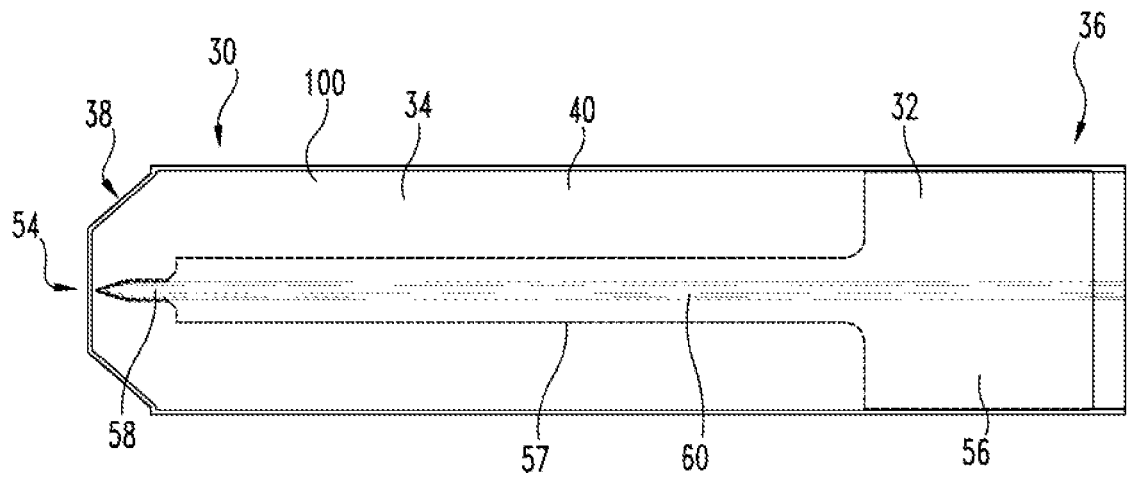
FIG. 9 is a bottom view of the FIG. 1 integrated device with a protective pull sheet.
Figure 10:
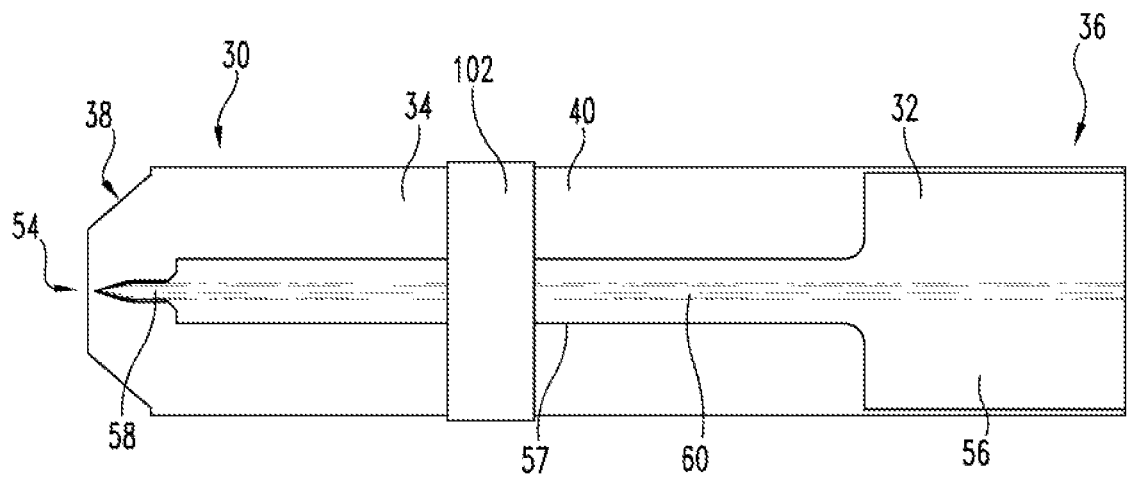
FIG. 10 is a bottom view of the FIG. 1 integrated device with a protective band.

Further, the integrated device 30, like the one shown in the drawings, can be easily packaged in a manner that reduces the chance of accidental injury, while at the same time maintains sterility. In one example (FIG. 9), the lancet 32 is sandwiched between the test strip 34 and a pull type protective sheet 100. The pull sheet 100 prevents the test strip 34 from bending, which in turn minimizes the chance of the lancet 32 extending and causing injury. Before use, the pull sheet 100 is pulled from the integrated device 30, thereby allowing the test strip 34 to bend during lancing. In another example (FIG. 10), a protective band 102 is wrapped around the test strip 34 and the lancet 32, which prevents the test strip 34 from bending prior to use.

While the invention has been illustrated and described in detail in the drawings and foregoing description, the same is to be considered as illustrative and not restrictive in character. It should be understood that only the preferred embodiment has been shown and described and that all changes and modifications that come within the spirit of the invention are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A method, comprising:
providing a lancet integrated test strip that includes a lancet attached to a test strip, wherein a cutting end of the lancet extends proximal a sampling end of the test strip that includes a sample chamber opening;
forming an incision in tissue with the lancet integrated test strip;
wherein said forming the incision includes bending the test strip by pressing the sampling end of the test strip against the tissue to extend the cutting end of the lancet past the sampling end of the test strip and into the tissue;
wherein the test strip includes a connector end located opposite the sample chamber opening, the lancet is attached to the test strip at the connector end;
wherein before said bending the test strip contacts the entire length of the lancet;
wherein during said bending a portion of the test strip between the sampling end and the connector end arches out of contact with the lancet; and
sampling fluid from the incision by drawing fluid into the sample chamber opening of the test strip.

2. The method of claim 1, further comprising:
analyzing the fluid from the incision with the test strip.

3. The method of claim 1, further comprising:
removing the lancet from the incision.

4. The method of claim 3, wherein said removing the lancet from the incision occurs before said sampling the fluid.

5. The method of claim 1, further comprising:
unbending the test strip prior to said sampling the fluid by moving the lancet away from the tissue.

6. The method of claim 1, wherein:
the cutting end of the lancet includes a u-shaped channel; and
said forming the incision includes cutting a u-shaped flap in the tissue with the cutting end of the lancet.

7. The method of claim 1, further comprising:
wherein the lancet integrated test strip is coupled to a holder;
wherein the holder has one or more stop surfaces; and
bracing the test strip with the stop surfaces when the test strip is bent.

8. The method of claim 1, further comprising:
wherein the test strip include a sample chamber, electrodes in the sample chamber, contact pads, and traces connecting the electrodes to the contact pads; and
wherein said bending the test strip includes bending at least the traces.

9. The method of claim 1, further comprising:
wherein the lancet is sandwiched between a protective pull type cover and the test strip; and
pulling the pull type protective cover from the test strip prior to said forming the incision.

10. The method of claim 1, further comprising:
wherein a protective band is wrapped around the test strip and the lancet; and
removing the protective band from the test strip and the lancet prior to said forming the incision.

11. The method of claim 1, further comprising:
wherein test strip includes a base substrate, a spacer layer, and a cover layer that together define a sample chamber that has the sample chamber opening; and
wherein the base substrate, spacer layer, and the cover layer all bend during said forming the incision.

12. The method of claim 1, further comprising:
wherein the lancet has a test strip attachment portion wherein the lancet is attached to the test strip; and wherein the lancet is unattached to the test strip from the test strip attachment portion to the cutting to allow bending of the test strip between the test strip attachment portion to the sample chamber opening during said forming the incision.

13. A method, comprising:
providing a lancet integrated test strip that includes a lancet attached to a test strip, wherein a cutting end of the lancet extends proximal a sampling end of the test strip that includes a sample chamber opening;
forming an incision in tissue with the lancet integrated test strip;
wherein said forming the incision includes bending the test strip by pressing the sampling end of the test strip against the tissue to extend the cutting end of the lancet past the sampling end of the test strip and into the tissue;
sampling fluid from the incision by drawing fluid into the sample chamber opening of the test strip;
wherein the test strip includes a connector end located opposite the sampling end;
inserting the lancet integrated test strip into a deflection cavity of a holder, wherein the holder has first and second stop surfaces that define the deflection cavity, wherein the first and second stop surfaces are obliquely angled in an opposite manner, wherein during said inserting the sampling end of the test strip is positioned at the first stop surface and the connector end of the test strip is positioned at the second stop surface;
wherein said bending the test strip includes bending the test strip in the deflection cavity over the length of the test strip from the sampling end to the connector end; and
limiting the degree to which the length of the test strip bends by bracing the test strip against the first and second stop surfaces in the deflection cavity.

14. The method of claim of claim 13, further comprising:
wherein the test strip includes electrode traces that are configured to bend as the test strip bends; and
wherein the first and second stop surfaces are configured to prevent excessive bending of the electrode traces.

15. The method of claim 13, further comprising:
wherein the test strip includes contact pads at the connector end, electrodes in the sample chamber, and electrode traces operatively coupling the electrodes to the contact pads;
wherein the test strip includes electrode traces that are configured to bend as the test strip bends;
wherein the first and second stop surfaces are configured to prevent excessive bending of the electrode traces;
wherein the lancet includes a test strip attachment portion attached to the test strip at the connector end directly underneath the contact pad;
coupling to the contact pads of the test strip to a meter; and
stiffening the contact pads with the test strip attachment portion so that the contact pads remain coupled with the meter during said bending of the test strip.

16. A method, comprising:
providing a lancet integrated test strip that includes a lancet attached to a test strip, wherein a cutting end of the lancet extends proximal a sampling end of the test strip that includes a sample chamber opening;
forming an incision in tissue with the lancet integrated test strip;
wherein said forming the incision includes bending the test strip by pressing the sampling end of the test strip against the tissue to extend the cutting end of the lancet past the sampling end of the test strip and into the tissue;
wherein the sample chamber opening moves relative to the lancet from a first position where the sample chamber opening extends past the cutting end of the lancet to a second position where the sample chamber opening is retracted relative to the cutting end of the lancet as the test strip bends during said forming the incision; and
sampling fluid from the incision by drawing fluid into the sample chamber opening of the test strip.

17. The method of claim 16, further comprising:
wherein the test strip includes a connector end located opposite the sample chamber opening, the lancet is attached to the test strip at the connector end;
wherein at the first position the test strip contacts along the entire length of the lancet; and
wherein at the second position a portion of the test strip between the sampling end and the connector end arches out of contact with the lancet.

18. A method, comprising:
providing a lancet integrated test strip that includes a lancet attached to a test strip, wherein a cutting end of the lancet extends proximal a sampling end of the test strip that includes a sample chamber opening;
forming an incision in tissue with the lancet integrated test strip;
wherein said forming the incision includes bending the test strip by pressing the sampling end of the test strip against the tissue to extend the cutting end of the lancet past the sampling end of the test strip and into the tissue;
wherein the cutting end of the lancet moves relative to the test strip from a first position where the sample chamber opening extends past the cutting end of the lancet to a second position where the cutting end of the lancet extends past the sample chamber opening as the test strip bends during said forming the incision; and
sampling fluid from the incision by drawing fluid into the sample chamber opening of the test strip.

* * * * *

UNITED STATES PATENT AND TRADEMARK OFFICE
CERTIFICATE OF CORRECTION

| | | |
|---|---|---|
| PATENT NO. | : 8,157,750 B2 | Page 1 of 1 |
| APPLICATION NO. | : 12/687920 | |
| DATED | : April 17, 2012 | |
| INVENTOR(S) | : Charles C. Raney et al. | |

It is certified that error appears in the above-identified patent and that said Letters Patent is hereby corrected as shown below:

Col. 11, line 36, replace "14. The method of claim of claim 13, further comprising:" with
--14. The method of claim 13, further comprising:--

Signed and Sealed this
Fifth Day of June, 2012

David J. Kappos
*Director of the United States Patent and Trademark Office*